United States Patent [19]

Rieber et al.

[11] Patent Number: 5,684,201
[45] Date of Patent: Nov. 4, 1997

[54] PREPARATION OF ALIPHATIC AND CYCLOALIPHATIC OXIMES

[75] Inventors: Norbert Rieber, Mannheim; Peter Lingelbach; Tom Witzel, both of Ludwigshafen; Ulrich Müller, Neustadt, all of Germany

[73] Assignee: BASF Aktiengesellschaft, Ludwigshafen, Germany

[21] Appl. No.: 492,906

[22] Filed: Jun. 20, 1995

[30] Foreign Application Priority Data

Jun. 23, 1994 [DE] Germany .............. 44 21 928.8

[51] Int. Cl.⁶ ................................. C07C 249/04
[52] U.S. Cl. .............. 564/267; 564/253; 564/268
[58] Field of Search ................ 564/253, 268, 564/267

[56] References Cited

U.S. PATENT DOCUMENTS

| | | | |
|---|---|---|---|
| 4,163,756 | 8/1979 | Armor | 260/566 A |
| 4,504,681 | 3/1985 | Armor | 564/267 |
| 5,026,911 | 6/1991 | Venturello et al. | 564/267 |
| 5,227,525 | 7/1993 | Tonti et al. | 564/268 |
| 5,239,120 | 8/1993 | Merger et al. | 564/454 |

FOREIGN PATENT DOCUMENTS

| | | |
|---|---|---|
| 43445 | 1/1982 | European Pat. Off. . |
| 208 311 | 1/1987 | European Pat. Off. . |
| 395 046 | 10/1990 | European Pat. Off. . |

OTHER PUBLICATIONS

*Chem. Abst.*, vol. 116, No. 2, Jan. 13, 1992, Abst. No. 8204d.

*Houben–Weyl*, vol. 7, part 2b, Keton II, p. 1947 (4th Edition 1976, Georg. Thieme Verlag Stuttgart).

Weissermel, Arpe, 3rd ed., VCH–Verlag, 1988, p. 270.

*Primary Examiner*—Peter O'Sullivan
*Attorney, Agent, or Firm*—Keil & Weinkauf

[57] ABSTRACT

Aliphatic or cycloaliphatic oximes are prepared by treating aliphatic or cycloaliphatic imines with oxygen or with an oxygen-containing gas in the presence of a catalyst.

6 Claims, No Drawings

PREPARATION OF ALIPHATIC AND CYCLOALIPHATIC OXIMES

The present invention relates to a process for the preparation of aliphatic and cycloaliphatic oximes.

Cyclohexanone oxime, which is known to be an important intermediate in the preparation of caprolactam, is usually prepared by reacting cyclohexanone with hydroxylamine salts. The salts obtained in large amounts in this procedure can be avoided, for example, by the hydroxylamine phosphate oxime (HPO) process (cf. Weissermel, Arpe, 3rd edition, VCH-Verlag, 1988, page 270 et seq.), in which buffer containing phosphoric acid is used. However, the preparation of the only moderately stable hydroxylamine is not avoided.

According to U.S. Pat. No. 4,163,756, cyclohexanone oxime can also be prepared by direct oximation with an ammonia/air mixture in the gas phase with selectivity of 51% for the oxime at a conversion of 54%. However, the disadvantage of this procedure is that the selectivities and conversions are too low for commercial use. Furthermore, the catalytic activity of the catalyst used is exhausted too rapidly owing to polymer formation.

According to EP-A 208,311, cyclohexanone is reacted in the liquid phase with hydrogen peroxide and ammonia to give the corresponding oxime, selectivity being 80% at a conversion of 95%. Owing to the high cost, however, the use of hydrogen peroxide is economically disadvantageous. The use of hydrogen peroxide is also disadvantageous for safety reasons.

EP-A 395,046 describes the oxidation of cyclohexylamine by direct oxidation in the liquid phase with homogeneous and heterogeneous titanium-containing catalysts. The selectivities achieved are up to 52% at conversions of 60%, with the result that the maximum yields are only 31.2%. Moreover, owing to the relatively expensive starting material cyclohexylamine, this procedure is disadvantageous also for economic reasons.

It is an object of the present invention to provide a process for the preparation of aliphatic or cycloaliphatic oximes which does not have the abovementioned disadvantages. In particular, it is intended to provide an economical process avoiding the known salt wastes.

We have found that this object is achieved by a process for the preparation of aliphatic or cycloaliphatic oximes by treating an aliphatic or cycloaliphatic imine with oxygen or with an oxygen-containing gas in the presence of a catalyst.

According to the invention, the aliphatic or cycloaliphatic imines are reacted with oxygen or with an oxygen-containing gas in the presence of a catalyst to give the corresponding oxime.

The aliphatic and cycloaliphatic imines used are in general imines of the general formula II

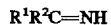 (II)

where $R^1$ is $C_1$–$C_{10}$-alkyl such as methyl, ethyl, n-propyl, isopropyl, n-butyl, sec-butyl, isobutyl, tert-butyl, n-pentyl, n-hexyl, n-heptyl, n-octyl, n-nonyl or n-decyl, and $R^2$ is hydrogen or $C_1$–$C_{10}$-alkyl such as methyl, ethyl, n-propyl, isopropyl, n-butyl, sec-butyl, isobutyl, tert-butyl, n-pentyl, n-hexyl, n-heptyl, n-octyl, n-nonyl or n-decyl, or $R^1$ and $R^2$ together are $C_3$–$C_{12}$-cycloalkylidene such as cyclopropylidene, cyclobutylidene, cyclopentylidene, cyclohexylidene, cycloheptylidene, cyclooctylidene, cyclononylidene, cyclodecylidene, cycloundecylidene or cyclododecylidene.

Examples of preferred imines are cyclopentylideneamine, cyclohexylideneamine (cyclohexanoneimine) and cycloheptylideneamine, particularly preferably cyclohexylideneamine (cyclohexanoneimine).

The imines are obtainable by processes which are known from the literature and are described, for example, in Houben-Weyl, Volume 7, Part 2b, Keton II, page 1947 (4th Edition 1976, Georg Thieme Verlag Stuttgart).

In a preferred embodiment (similar to the process from EP-A 449 111), the cycloaliphatic imines are prepared by imination of the corresponding cycloaliphatic ketones. Here, the corresponding cycloalkanones are generally reacted with excess ammonia at from 20° to 150° C., preferably from 30° to 130° C., particularly preferably from 50° to 100° C., and from 15 to 500, preferably from 100 to 350, bar in the presence of acidic heterogeneous catalysts to give the corresponding cycloalkylideneamines.

Suitable acidic heterogeneous catalysts are metal compounds having a Lewis acid or Bransted acid character, such as alumina, silica, titanium dioxide and zirconium dioxide, and phosphates, such as aluminum phosphates, and silicates, such as amorphous or crystalline aluminosilicates. Alumina, titanium dioxide, zirconium dioxide and silica are preferably used, in particular alumina and titanium dioxide. The acidity of the catalysts can, if required, be increased by doping with halides. For example, halogen-doped catalysts, such as chloride on alumina or chloride on titanium dioxide, are also used.

In the preferred imination, a catalyst space velocity of from 0.01 to 10, preferably from 0.05 to 7, particularly preferably from 0.1 to 5, kg of cycloalkanone per kg of catalyst per hour is as a rule maintained.

The amount of ammonia is usually chosen in the range from 5 to 500, preferably from 10 to 400, particularly preferably from 20 to 300, mole of ammonia per mole of cycloalkanone.

The use of a solvent, such as an alkanol or tetrahydrofuran, is optional.

The preferred imination may furthermore be carried out either continuously or batchwise but is preferably effected continuously, for example in pressure-resistant containers or cascades of pressure-resistant containers. In a particularly preferred embodiment, the cycloalkanone and ammonia are passed through a tube reactor in which the imination catalyst is arranged in the form of a fixed bed.

The reaction time in the imination depends essentially on the catalyst space velocity and on the amount of ammonia used. It is as a rule from 0.5 to 120, preferably from 1 to 40, particularly preferably from 1.5 to 20, minutes.

In the reaction of the imines with oxygen to give the corresponding oximes, as a rule a molar ratio of imine to oxygen of from 0.1 to 100, preferably from 1 to 10, is chosen. The oxygen-containing gas used is usually air, the same molar ratio of imine to oxygen generally being chosen. Other oxygen-containing gas mixtures may also be used, provided that the gases which do not contain oxygen are inert with respect to the other reactants.

The catalysts used are usually titanium-, zirconium- and/or hafnium-containing compounds in the form of their salts and oxides and organometallic compounds, with the exception of catalysts of the general formula I

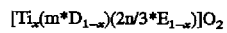 (I)

where D is silicon or germanium, E is cerium or aluminum and x is from 0.06 to 0.9 and m is 1 when n is 0 or m is 0 when n is 1. Suitable catalysts and their preparation have been described in detail in EP-A 395 046. Preferred catalysts are Ti(OEt)$_4$, Ti(O—iPr)$_4$, Ti(OBu)$_4$, Zr(OEt)$_4$, Zr(O—iPr)$_4$ and Zr(OBu)$_4$, particularly preferably Ti(OEt)$_4$, Ti(O—iPr)$_4$, Ti(OBu)$_4$ and Zr(OEt)$_4$.

The amount of catalyst is usually chosen in the range from 0.001 to 10, preferably from 0.1 to 2,% by weight, based on imine used.

The oximation may be carried out in the presence or absence of a solvent. The reaction is preferably carried out in a solvent which is inert with respect to oxygen. Examples are aromatic hydrocarbons, if desired halogenated, such as chlorobenzene, benzene, dichlorobenzene, toluene or xylene, preferably chlorobenzene.

The weight ratio of solvent to imine is chosen as a rule in the range from 50:1 to 1:1, preferably from 10:1 to 2:1.

In a further preferred embodiment, the oximation of the imine is carried out in the presence of the corresponding ketone. For example, the oximation of cyclohexylideneamine can be carried out in the presence of cyclohexanone. This procedure is advantageous because, in the preparation of the imine from the corresponding ketone, it is not essential to isolate the ketone before the oximation.

The reaction temperature is chosen in general in the range from 20° to 200° C., preferably from 50° to 150° C.

The pressure during the reaction is chosen as a rule in the range from 100 to 50,000, preferably from 3,000 to 10,000, kPa.

The reaction is usually carried out in the liquid phase. In principle, the reaction may also be effected in the gas or liquid/gas phase.

Of course, the reaction time depends essentially on the reaction parameters chosen and is usually from 1 to 100, preferably from 5 to 20, hours in the batchwise procedure.

After the oximation, the reaction mixture is usually worked up by a method known per se, such as distillation or extraction.

In a further preferred embodiment, the aliphatic or cycloaliphatic oximes are advantageously prepared by first preparing the imine from the corresponding ketone and then subjecting the imine-containing reaction mixture to the oximation, ie. carrying out the following steps:

a) imination of an aliphatic or cycloaliphatic ketone and
b) oxidation of the imine obtained in stage a) to give the corresponding oxime.

This preferred procedure has the advantage that, on the basis of observations to date, the imine to be oximated is substantially free of troublesome byproducts obtained by degradation of the imine.

The cyclohexanone oxime obtainable in the novel process can be converted into caprolactam by known processes (cf. for example, Weissermel, Arpe, 3rd edition, VCH-Verlag, 1988, page 270 et seq.).

Compared with the prior art processes, the novel process has the advantages that salt wastes and expensive and unsafe starting materials are avoided and air available free of charge can be used as the oxidizing agent.

EXAMPLES

The characterization of the substances and the determinations of the conversions and selectivities were carried out by gas chromatography.

Preparation of cyclohexanoneimine (similarly to EP-A 449 111)

Example 1

39.2 g (0.4 mol) of cyclohexanone and 120 g (200 ml; 7.2 mol) of liquid ammonia per hour were pumped upward from below through a tube reactor (diameter: 16 mm, height of fill: 50 cm, oil-heated double jacket) which had been filled with 63.5 g (100 ml) of titanium dioxide (anatase) in the form of 1.5 mm extrudates, at 100 bar and 80° C. Thereafter, 400 ml of chlorobenzene were introduced, the ammonia was removed by distillation and the aqueous phase was separated off. After drying of the organic phase, a 10% strength by weight solution of cyclohexanoneimine in chlorobenzene was obtained in a yield of 95%.

Example 2

39.2 g (0.4 mol) of cyclohexanone and 120 g (200 ml; 7.2 mol) of liquid ammonia per hour were pumped upward from below through a tube reactor (diameter: 16 mm, height of fill: 50 cm, oil-heated double jacket) which had been filled with 64.4 g (92 ml) of gamma-alumina in the form of 1.5 mm extrudates, at 100 bar and 80° C. Thereafter, 400 ml of chlorobenzene were introduced, the ammonia was removed by distillation and the aqueous phase was separated off. After drying of the organic phase, a 10% strength by weight solution of cyclohexanoneimine in chlorobenzene was obtained in a yield of 92%.

Example 3

Air was added to 10 g of cyclohexylideneamine (cyclohexanoneimine), 100 ml of chlorobenzene and 1 g of tetrakis(n-butoxy) titanate in a 300 ml stirred autoclave, the oxygen partial pressure being 5,000 kPa, and the mixture was heated to 100° C. The reaction was terminated after 20 hours. At a conversion of 100%, the selectivity was 46%, based on imine used.

The starting compounds stated in the table below, in the amounts stated there, were converted into the corresponding oximes under the reaction conditions stated there, this being effected similarly to Example 3. The calculated selectivities are likewise shown in this table.

TABLE

| Example | Temp [° C.] | Pressure [bar] | Time [h] | Catalyst [1% by wt.] | Cyclohexanone [% by weight] | Cyclohexanoneimine [% by weight] | Cyclohexanone [% by weight] | Cyclohexanoneimine [% by weight] | Cyclohexanone oxime [% by weight] | Cyclohexanone oxime selectivity [%] |
| --- | --- | --- | --- | --- | --- | --- | --- | --- | --- | --- |
| according to the invention | | | | | Feed | | Discharge | | | |
| 3 | 100 | 50 | 20 | Ti(OEt)$_4$ | 0 | 3.38 | 0.20 | 0 | 1.56 | 46 |
| 4 | 100 | 50 | 20 | Ti(OEt)$_4$ | 0.78 | 3.38 | 0.86 | 0 | 1.64 | 49 |
| 5 | 100 | 50 | 43 | Zr(Oi—Pr)$_4$ | 0.99 | 4.38 | 1.10 | 0 | 1.91 | 44 |
| 6 | 100 | 50 | 5 | Ti(Oi—Pr)$_4$ | 0.71 | 5.79 | 2.42 | 0 | 1.30 | 22 |

TABLE-continued

| Example | Temp [°C.] | Pressure [bar] | Time [h] | Catalyst [1% by wt.] | Cyclohexanone [% by weight] | Cyclohexanoneimine [% by weight] | Cyclohexanone [% by weight] | Cyclohexanoneimine [% by weight] | Cyclohexanone oxime [% by weight] | Cyclohexanone oxime selectivity [%] |
|---|---|---|---|---|---|---|---|---|---|---|
| 7 | 100 | 50 | 12 | Zr(OEt)$_4$ | 9.01 | 6.21 | 7.62 | 0 | 1.24 | 20 |
| 8 for comparison | 100 | 50 | 19 | Ti(OBu)$_4$ | 1.03 | 3.02 | 1.80 | 0 | 0.07 | 2 |
| 9 | 100 | 50 | 1 | TiO$_2$ | 5.34 | 10.96 | 10.67 | 0 | 0 | 0 |
| 10 | 100 | 50 | 4 | without catalyst | 6.72 | 10.13 | 8.88 | 2.77 | 0 | 0 |
| 11 | 100 | 50 | 21 | without catalyst | 6.72 | 10.13 | 8.49 | 0 | 0 | 0 |

We claim:

1. A process for the preparation of an aliphatic or cycloaliphatic oxime, wherein an aliphatic or cycloaliphatic imine is treated with oxygen or with an oxygen-containing gas in the presence of a member selected from the group consisting of a titanium, zirconium and hafnium-containing compound, or the salts, oxides and organometallics of these compounds, with the exception of a catalyst of the formula I

$$[Ti_x(m*D_{1-x})(2n/3*E^{1-n})]O_2 \quad (I)$$

where D is silicon or germanium, E is cerium or aluminum and x is from 0.06 to 0.9 and mm is 1 when n is 0 or m is 0 when n is 1.

2. A process as claimed in claim 1, wherein the catalyst used is selected from the group consisting of Ti(OR)$_4$, Zr(OR)$_4$ and Hf(OR)$_4$, where R is $C_1$–$C_{10}$-alkyl.

3. A process as claimed in claim 1, wherein a $C_4$-$C_{13}$-cycloalkanoneimine is used.

4. A process as claimed in claim 3, wherein the cycloalkylideneamine used is cyclohexanoneimine.

5. A process as claimed in claim 1, wherein the reaction is carried out in the presence of the corresponding ketone.

6. A process for the preparation of an aliphatic or cycloaliphatic oxime, wherein the following steps are carried out:

a) imination of an aliphatic or cycloaliphatic ketone with ammonia in a manner known per se and b) oxidation of the imine obtained in stage a) with oxygen or with an oxygen-containing gas in the presence of a member selected from the group consisting of a titanium, zirconium and hafnium-containing compound, or the salts, oxides and organometallics of these compounds, with the exception of a catalyst of the formula I

$$[Ti_x(m*D_{1-x})(2n/3*E^{1-n})]O_2 \quad (I)$$

where D is silicon or germanium, E is cerium or aluminum and x is from 0.06 to 0.9 and m is 1 when n is 0 or m is 0 when n is 1, to give the corresponding oxime.

* * * * *